(12) United States Patent
Doan et al.

(10) Patent No.: US 7,031,774 B1
(45) Date of Patent: Apr. 18, 2006

(54) SWITCH FOR ELECTRODE SELECTIONS IN SINGLE-PASS ATRIAL/VENTRICULAR LEADS

(75) Inventors: Phong D. Doan, Stevenson Ranch, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 678 days.

(21) Appl. No.: 10/236,303

(22) Filed: Sep. 5, 2002

Related U.S. Application Data

(63) Continuation of application No. 09/689,478, filed on Oct. 11, 2000, now abandoned.

(51) Int. Cl.
*A61N 1/18* (2006.01)

(52) U.S. Cl. .......................... 607/37; 607/38; 607/119; 607/122; 607/123

(58) Field of Classification Search ................. 607/37, 607/38, 122–123, 119; 600/374, 375
See application file for complete search history.

(56) References Cited

U.S. PATENT DOCUMENTS

| | | | |
|---|---|---|---|
| 3,817,241 A | 6/1974 | Grausz | 128/2.06 E |
| 4,479,500 A | 10/1984 | Smits | 128/786 |
| 4,602,645 A | 7/1986 | Barrington et al. | 128/786 |
| 5,273,053 A | 12/1993 | Pohndorf | 607/132 |
| 5,431,696 A | 7/1995 | Atlee, III | 607/124 |
| 5,578,067 A | 11/1996 | Ekwall et al. | 607/122 |
| 5,584,874 A | 12/1996 | Rugland et al. | 607/132 |
| 5,755,763 A | 5/1998 | Farfel | 607/122 |
| 5,824,030 A * | 10/1998 | Yang et al. | 607/122 |
| 5,824,031 A | 10/1998 | Cookston et al. | 607/122 |
| 5,919,222 A | 7/1999 | Hjelle et al. | 607/122 |
| 5,957,968 A | 9/1999 | Belden et al. | 607/126 |
| 6,021,355 A | 2/2000 | Shchervinsky | 607/132 |
| 6,295,475 B1 * | 9/2001 | Morgan | 607/122 |

* cited by examiner

*Primary Examiner*—Robert E. Pezzuto
*Assistant Examiner*—Jessica L. Reidel

(57) ABSTRACT

An implantable electrical lead for electrical sensing and stimulation of the heart includes a lead body which includes a ventricular tip, a pair of distal atrial ring electrodes, a pair of proximal atrial ring electrodes, a pair of first stationary contacts in electrical continuity, respectively, with the distal atrial ring electrodes, and a pair of second stationary contacts in electrical continuity, respectively, with the proximal atrial ring electrodes. A bifurcation boot overlies the lead and is slidable lengthwise of the lead body. The bifurcation boot carries first and second mobile contacts movable between first and second longitudinally spaced positions on the lead body. In the first position, the first and second mobile contacts are engaged with the first pair of the stationary contacts, respectively. In the second position, the first and second mobile contacts are engaged with the second pair of the stationary contacts, respectively. Stop members integral with the lead body and engaged by the bifurcation boot establish the first and second positions.

18 Claims, 4 Drawing Sheets

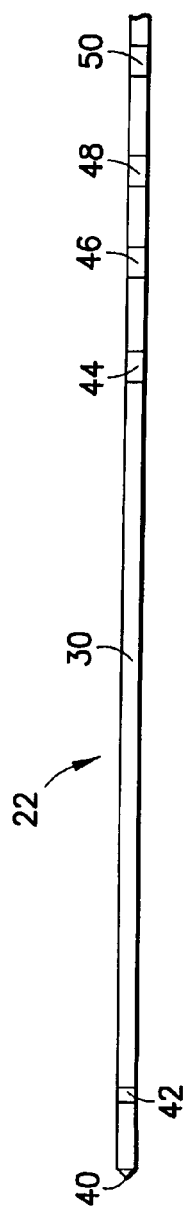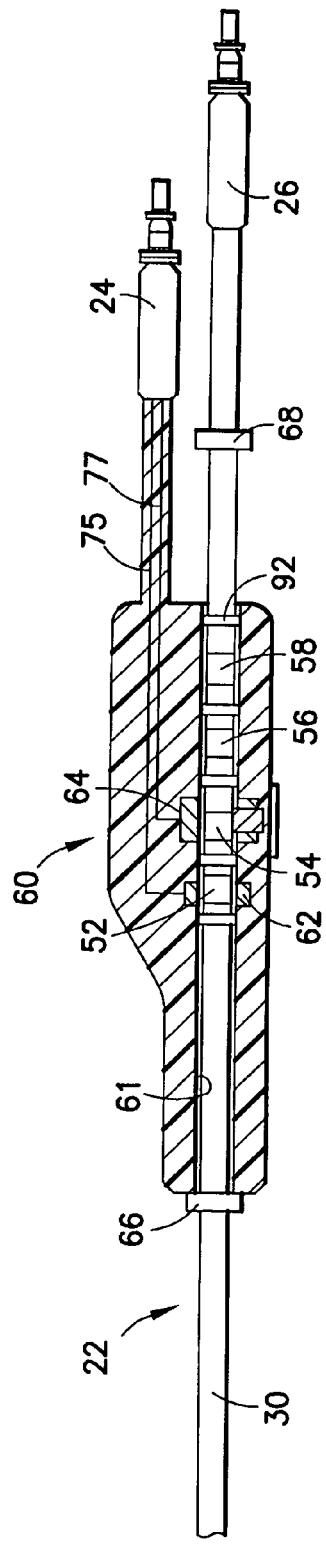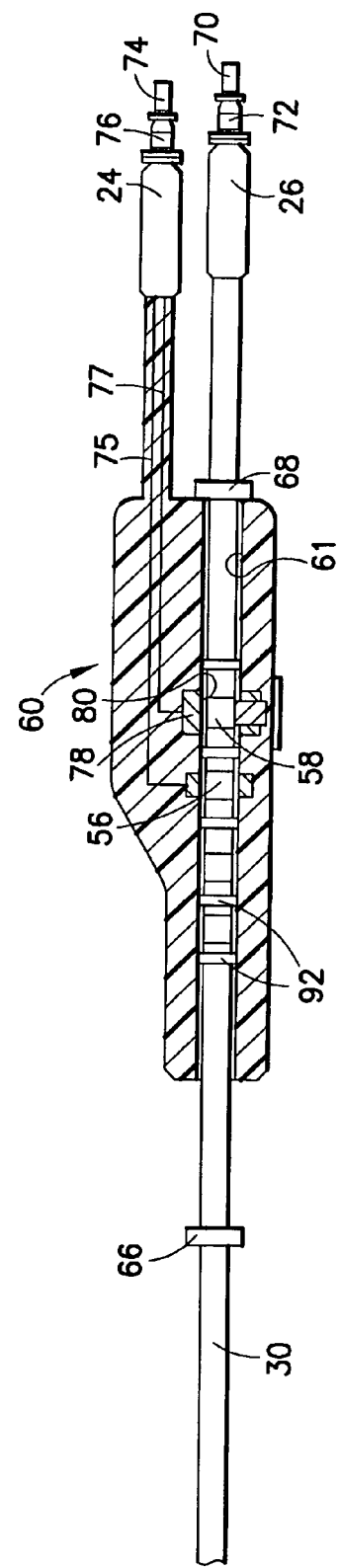

SWITCH FOR ELECTRODE SELECTIONS IN SINGLE-PASS ATRIAL/VENTRICULAR LEADS

CROSS-REFERENCE TO RELATED APPLICATIONS

This application is a continuation of U.S. patent application Ser. No. 09/689,478, filed Oct. 11, 2000, now abandoned.

FIELD OF THE INVENTION

The present invention relates generally to lead assemblies for connecting implantable medical devices with selected body tissue to be stimulated by such devices, and more particularly to a lead assembly construction which is compatible to different sizes of hearts.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers or defibrillators for providing precisely controlled stimulation, cardioversion or defibrillation, pulses to the heart. The appended claims are not intended to be limited, however, to any specific example or embodiment described herein.

Implantable pacemaker or defibrillation leads form the electrical connection between the implanted cardiac pacemaker pulse generator or defibrillator and the heart tissue which is to be stimulated. As is well known, the leads connecting such pacemakers with the heart may be used for stimulation or for sensing electrical signals produced by the heart or for both stimulation and sensing in which case a single lead serves as a bi-directional pulse transmission link between the pacemaker and the heart. A transvenous endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled or wound conductor or cable surrounded by an insulating tube or sheath couples the connector pin at the proximal end with the electrode at the distal end.

For a Single-pass Atrial/Ventricular (SPAV) lead, the lead is intended to be placed with its distal tip in the right ventricle or in veins overlying the left ventricle, for stimulation and sensing in both ventricles and atria. On a typical bipolar SPAV lead, at minimum, there are typically two sets of electrodes. The first set of two electrodes is located at the distal tip for ventricular stimulation and sensing. The second set of two electrodes would be located in the atrium and proximally from the ventricular electrodes for atrial stimulation and sensing. Due to different sizes of hearts, it is difficult to determine a distance between the first and second set of the electrodes. Picking the wrong distance can result in the atrial electrodes being in a less optimal location in the atrium or ventricle, further resulting in insufficient stimulation and/or sensing performance. One of the current solutions is to have more than one set of electrodes on the lead body. Each set of the electrodes is connected to a bipolar connector. At implant, the implanter would choose the proper set of the electrodes for that particular patient. This approach is acceptable but there is a huge drawback. At the end of the implant, the extra connectors of the unused electrode sets must be either cut-off or capped-off. In order to solve the problem of having the extra connectors, the invention described below will provide a method of using only one connector, which could work with two or more sets of the electrode pairs.

Typical of prior art disclosures is U.S. Pat. No. 5,919,222 to Hjelle et al. which discloses an adjustable medical electrode lead with a wide degree of adjustability and flexibility with regard to the locations and length of its cardioversion/defibrillation electrodes. This is accomplished by means of a single elongated defibrillation electrode over which one or more sliding sheaths is located, each of the sheaths having a length less than that of the electrode itself. By this mechanism, movement of the sheath or sheaths relative to the electrode can be used to provide for single or multiple electrode surfaces and to vary the location and length of those surfaces along the length of the lead.

U.S. Pat. No. 5,584,874 to Rugland et al. discloses a medical electrical lead with an anchoring sleeve having a series of circumferential suture grooves at longitudinally spaced locations to accommodate different sizes of patients.

U.S. Pat. No. 5,578,067 to Ekwall et al. discloses an electrode apparatus with which the distance between the electrodes on an electrode cable can be changed in a very simple manner and in which the surface area exposed to tissue of at least one electrode can be enlarged, reduced and even rotated around the electrode cable in certain instances.

U.S. Pat. No. 4,602,645 to Barrington et al. discloses a cardiac pacing catheter system which includes a main guiding catheter and a pair of electrical leads adapted to make direct electrical contact with the ventricle and the atrium of the patient's heart. Each of the leads can be advanced and manipulated separately within the main catheter body to accommodate different sizes of hearts.

U.S. Pat. No. 5,578,067 to Ekwall et al. discloses a single-pass atria-ventricular lead for transvenous insertion. An adjustment device to accommodate the size of the patient is provided to allow axial adjustment of the ventricular lead sheath relative to the atrial lead sheath without modification to or adjustment of the connector assembly prior to attachment of an implantable pulse generator.

It was in light of the foregoing that the present invention was conceived and has now been reduced to practice.

SUMMARY OF THE INVENTION

The present invention relates to an implantable electrical lead for electrical sensing and stimulation of the heart includes a lead body which, when implanted, extends into the right ventricle or through the coronary sinus vein and into one of the coronary veins overlying the left ventricle via the right atrium. The electrical lead includes a ventricular tip electrode at a distal end for engagement with ventricular cardiac tissue of the heart and a ventricular ring electrode spaced from the ventricular tip electrode, a pair of distal atrial rings positioned within the right atrium or the coronary sinus vein are proximal to the tip and ring electrode, a pair of proximal atrial rings positioned within the right atrium or the coronary sinus vein proximal to the distal atrial rings, a pair of first stationary contacts in electrical continuity, respectively, with the distal atrial rings, and a pair of second stationary contacts in electrical continuity, respectively, with the proximal atrial rings. A bifurcation boot overlies the lead and is slidable lengthwise of the lead body. The bifurcation boot carries first and second mobile contacts movable between first and second longitudinally spaced positions on the lead body. In the first position, the first and second mobile contacts are engaged with the first pair of the stationary contacts, respectively. In the second position, the first and second mobile contacts are engaged with the second pair of the stationary contacts, respectively. Stop members integral with the lead body and engaged by the bifurcation boot establish the first and second positions.

According to the invention, a switch is located in the bifurcation boot area used to change the electrical connection between the atrial bipolar connector and the sets of the atrial electrodes. In a typical construction, a SPAV lead would have two sets of the atrial electrodes. During the lead implant procedure, once the lead is implanted into the right ventricle or into the coronary veins overlying the left ventricle, with acceptable ventricular stimulation thresholds and sensing amplitudes, the stimulation and sensing in the atrium would be tested at the pre-set pair of the atrial electrodes. If the test data from the pre-set pair of the atrial electrodes is not acceptable, the implanter would unfasten the set-screw on the bifurcation boot which is used to anchor the bifurcation boot at the pre-set location.

In the system of the invention, a spring contact and setscrew combination is used to provide the electrical connection between the atrial rings and the connector contacts. Once the set-screw is unfastened, the implanter simply slides the bifurcation boot against the other stopper in order to change the electrical connection of the atrial connector from the pre-set atrial electrodes to a second set of the atrial electrodes.

A primary feature, then, of the present invention is the provision of a lead assembly for connecting implantable medical devices with selected body tissue to be stimulated by such devices wherein the lead assembly construction is compatible to different sizes of hearts.

Another feature of the present invention is the provision of such a lead assembly construction, which allows any dual chamber pulse generator to be used with the leads.

Still another feature of the present invention is the provision of such a lead assembly construction, which allows physicians to choose the most optimal electrode set for the intended therapies.

Yet another feature of the present invention is the provision of such a lead assembly construction which enables only one lead to be used for different hearts.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 3 is a side elevation view of an electrical lead which is an integral component of the invention;

FIGS. 4 and 5 are a detail side elevation views, each partly cut away and shown in section, of a bifurcation boot with mobile contacts in position on the electrical lead of FIGS. 1 and 2, depicting two positions according to the invention;

DETAILED DESCRIPTION OF THE PREFERRED EMBODIMENT

Figure 1:
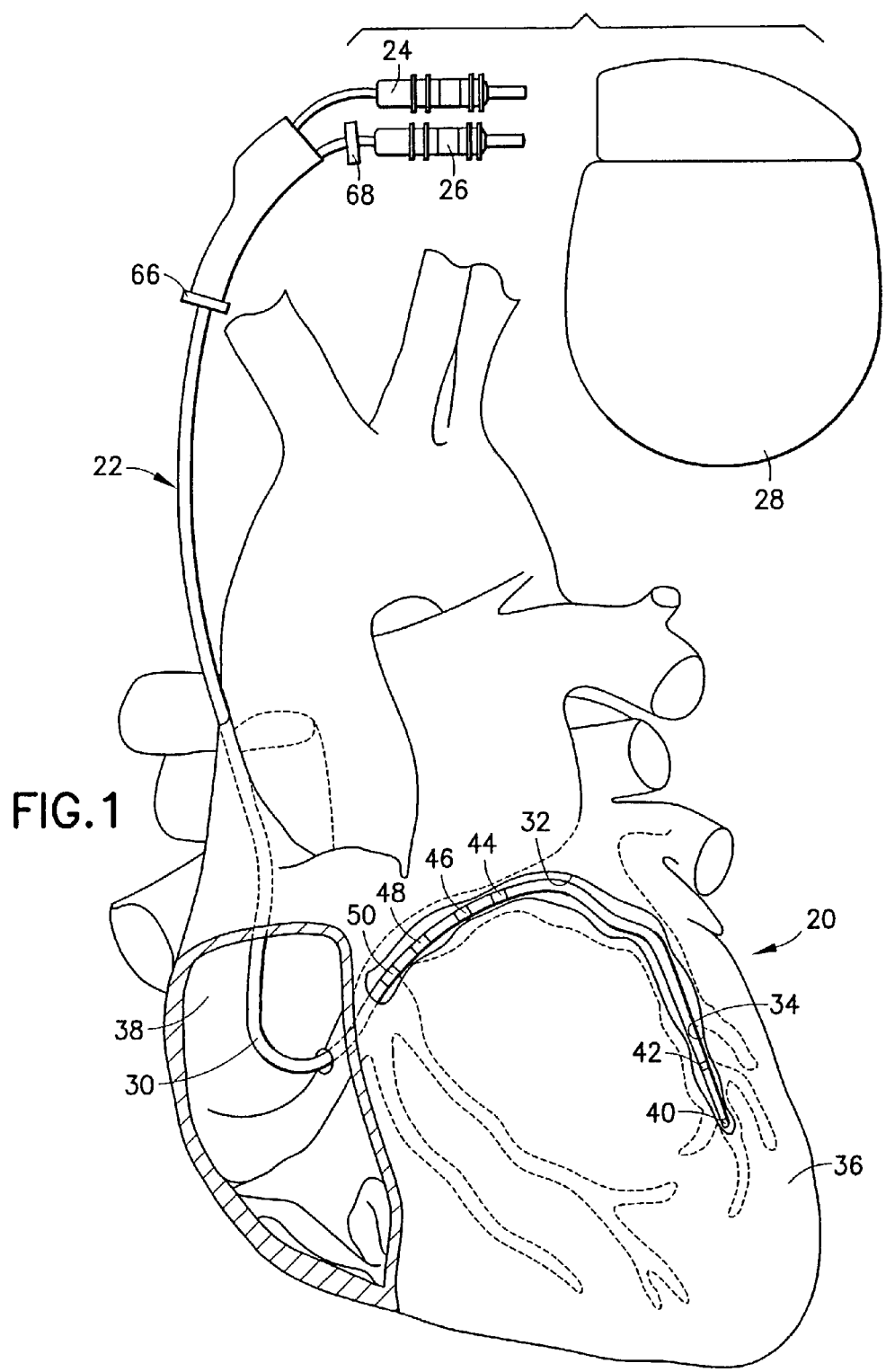
FIG. 1 is a diagrammatic elevation view of a heart, partially cut away, in which is implanted an electrical lead modified according to the invention, for connection to an electrical stimulation device.
Figure 2:
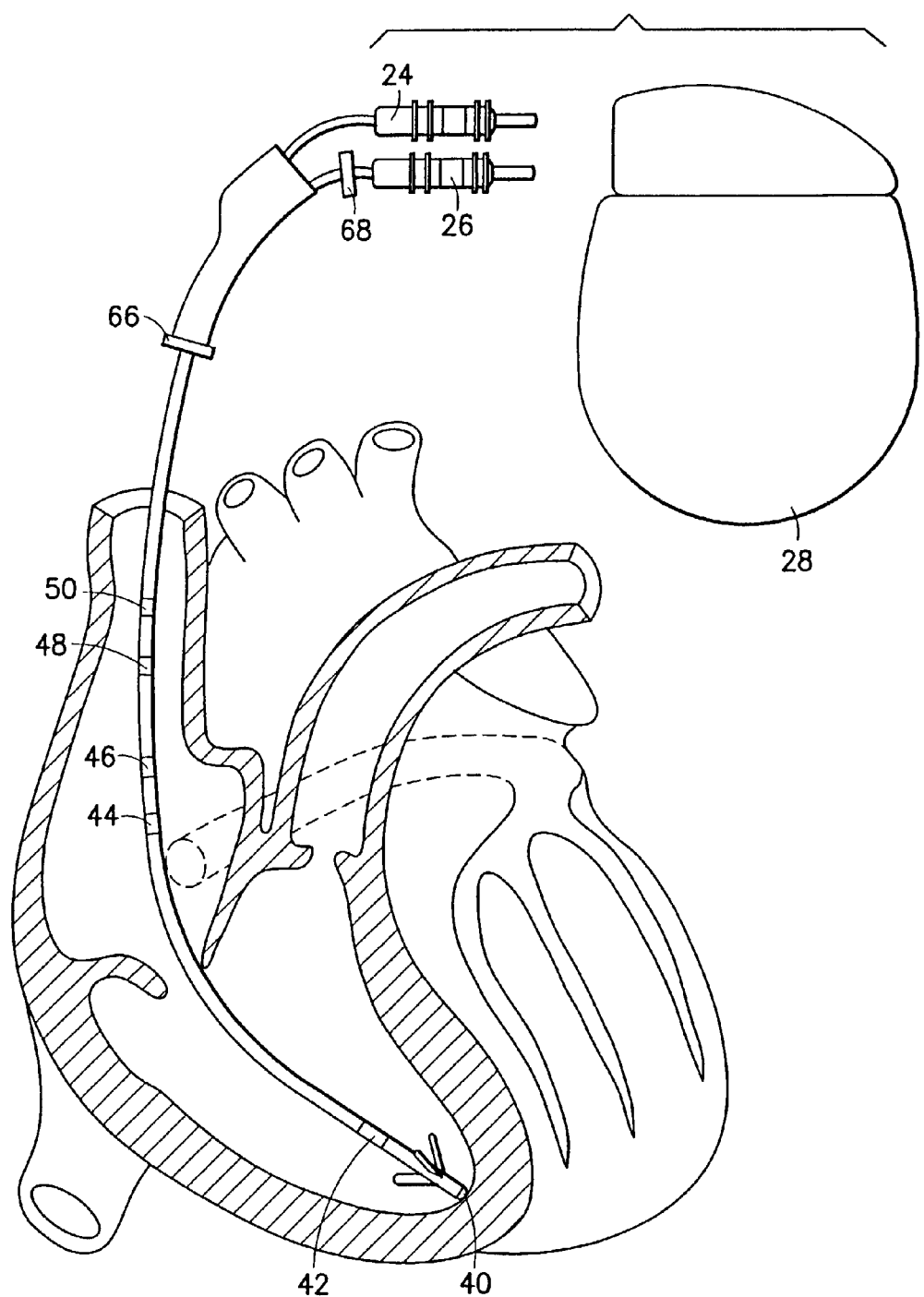
FIG. 2 is an elevation view of a portion of the implantable electrical lead illustrated in FIG. 1.

Referring to FIGS. 1 and 2, there are shown diagrammatic elevation views of a heart 20, partially cut away, in which is implanted an electrical lead 22, embodying the invention. The electrical lead 22 is connectable by means of connectors 24, 26 to an electrical stimulation device such as an implantable pacemaker or defibrillator 28. Although the present invention will be described with reference to the single embodiment shown in the drawings, it should be understood that the present invention can be embodied in many alternate forms of embodiments. In addition, any suitable size, shape, number or type of elements or materials could be used.

Viewing also FIG. 3, the implantable electrical lead 22 is employed in combination with the implantable pacemaker or defibrillator 28 for electrical sensing and stimulation of the heart 20. Lead 22 includes a lead body 30 which, when implanted, extends through the coronary sinus vein 32 and into one of the coronary veins 34 overlying the left ventricle 36. The lead body 30 is advanced via the right atrium 38 and includes a ventricular tip electrode 40 at a distal end for engagement with ventricular tissue of the heart and a ventricular ring electrode 42 spaced from the ventricular tip electrode.

With continuing reference to FIGS. 1, 2 and 3, a pair of distal atrial rings 44, 46 are positioned within the coronary sinus vein 32. As such, the distal atrial rings 44, 46 are proximal to the tip and ring electrodes 40, 42, respectively, located in a coronary vein 34 overlying the left ventricle 36. A pair of proximal atrial rings 48, 50, spaced from the distal atrial rings 44, 46, are also positioned within the coronary sinus vein 32 but proximal to the distal atrial rings.

Turning now to FIGS. 4 and 5, distant from the distal atrial rings 44, 46 and from the proximal atrial rings 48, 50 and nearer to the connectors 24, 26 are a pair of first stationary contacts 52, 54 in electrical continuity, respectively, with the distal atrial rings 44, 46 and a pair of second stationary contacts 56, 58 in electrical continuity, respectively, with the distal atrial rings 48, 50. An elongated bifurcation boot 60 has a longitudinally extending passage 61 therethrough for the slidable reception lengthwise of the lead body 30 and actually overlies the lead body 30.

The bifurcation boot 60 carries first and second mobile contacts 62, 64, respectively, and is movable between first (see FIG. 4) and second (see FIG. 5) longitudinally spaced positions on the lead body 30. In the first position of the bifurcation boot 60, the first and second mobile contacts 62, 64 are engaged with the first pair of the stationary contacts, 52, 54, respectively, and in its second position, the first and second mobile contacts are engaged with the second pair of the stationary contacts, 56, 58, respectively. A first stop member in the form of a distal ring 66 projects radially away from an outer peripheral surface of the lead body 30, is located distally of the bifurcation boot 60, and is integral with the lead body 30. When engaged by the bifurcation boot 60, the distal ring 66 establishes the first position at which the first and second mobile contacts 62, 64 are engaged with the first pair of the stationary contacts 52. 54. In a similar fashion, a second stop member in the form of a proximal ring 68 projects radially away from an outer peripheral surface of the lead body 30, is located proximally of the bifurcation boot 60, and is integral with the lead body 30. When engaged by the bifurcation boot 60, the distal ring 68 establishes the second position at which the first and second mobile contacts 62, 64 are engaged with the second pair of the stationary contacts 56, 58. Preferably, a transverse dimension of the lead body 30 is only slightly smaller than that of the longitudinally extending passage 61.

With continuing reference to FIGS. 4 and 5, the lead body 30 includes the ventricular connector 26 at its proximal end including a first terminal contact 70 in electrical continuity with the ventricular tip electrode 40 and a second terminal contact 72 in electrical continuity with the ventricular ring electrode 42. For its part, the bifurcation boot 60 includes the atrial connector 24 at its proximal end including a first terminal contact 74 in electrical continuity with the first mobile contact 62 by a first conductor 75 and a second terminal contact 76 in electrical continuity with the second mobile contact 64 by a second conductor 77.

Figure 5A:
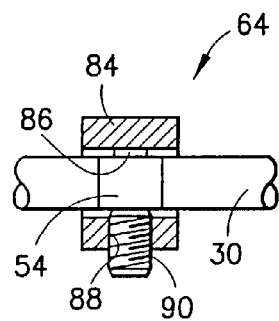
FIG. 5A is a detail elevation view, partly in section, illustrating one mobile contact of the bifurcation boot illustrated in FIGS. 4 and 5.
Figure 6:
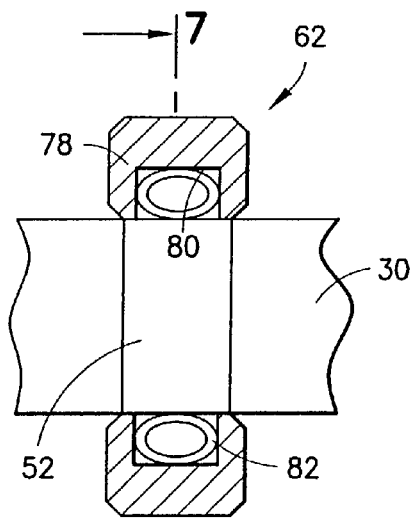
FIG. 6 is a detail elevation view, partly in section, illustrating another mobile contact of the bifurcation boot illustrated in FIGS. 4 and 5.
Figure 7:
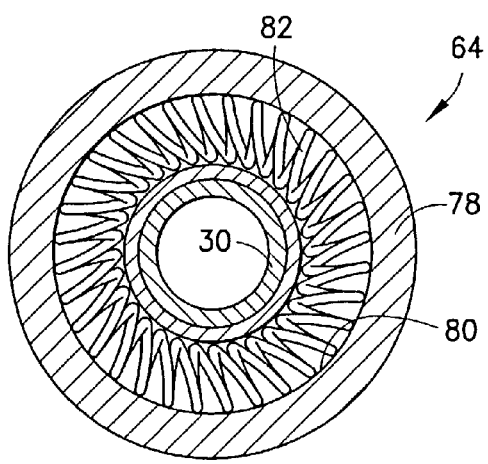
FIG. 7 is a cross section view taken generally along line 7—7 in FIG. 6.

With continued reference to FIGS. 4 and 5 and attention now also to FIGS. 5A, 6 and 7, the first mobile contact 62 includes an annular track member 78 fixed on the bifurcation boot 60 at a location longitudinally spaced from the second mobile contact 64. The first mobile contact 62 has an annular recess 80 and a coil spring 82 received in the annular recess. Viewing especially FIG. 5A, the second mobile contact 64 includes an annular locking member 84 fixed on the bifurcation boot 60 encircling the lead body 30. The annular locking member 84 has an inner peripheral surface 86 spaced from the outer peripheral surface of the lead body, a radially directed tapped bore 88, and a setscrew 90 threadedly received in the tapped bore.

With this construction, when the bifurcation boot 60 in a first position (FIG. 4), the setscrew 90 of the second mobile contact 64 can be advanced from a withdrawn position to a position engaged with one of the pair of second stationary contacts, namely, with contact 54 while the coil spring 82 of the first mobile contact 62 is engaged with the other of the pair of first stationary contacts, namely, with contact 52. At this time, the engagement of the setscrew 90 with the contact 54 releasably prevents movement of the bifurcation boot 60 from the first position.

In a similar manner, when the bifurcation boot 60 is in the second position (FIG. 5), the setscrew 90 of the second mobile contact 64 can be advanced from the withdrawn position to the position engaged with one of the pair of second stationary contacts, namely, with contact 58 while the coil spring 82 of the first mobile contact 62 is engaged with the other of the pair of first stationary contacts, namely, with contact 56. At this time, the engagement of the setscrew 90 with the contact 58 releasably prevents movement of the bifurcation boot 60 from the second position.

Again referring to FIGS. 4 and 5, the electrical lead 22 includes a plurality of seal members 92 contiguously encircling the outer surface of the lead body 30 at longitudinally spaced and strategically positioned locations. The seal members are engaged with the longitudinally extending passage 61 of the bifurcation boot 60 to prevent fluid from reaching the stationary contacts 52, 54, 56, 58 and the mobile contacts 62, 64. In this regard, each of the stationary contacts on the lead body is positioned between a pair of the seal members.

Figure 8:
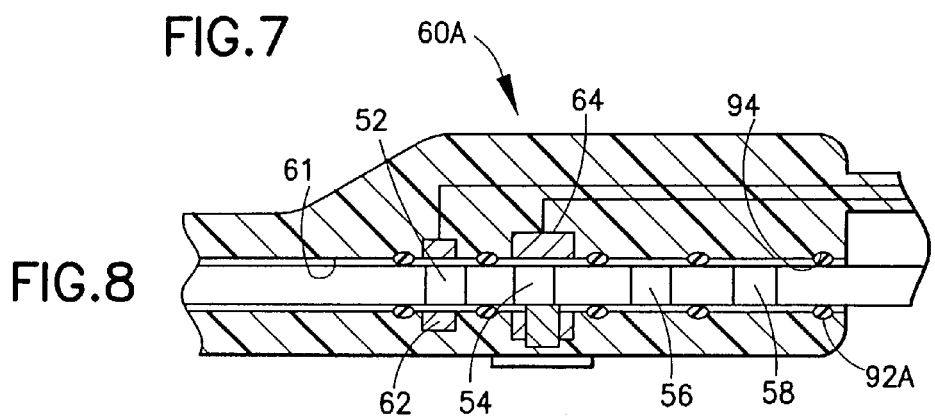
FIG. 8 is a side elevation view of a bifurcation boot with the insulation seal member integrally included in the boot.

The seal members which are preferably O-rings and are electrically insulative could alternatively be provided on the bifurcation boot rather than on the lead body, or in addition to, being on the lead body. In this instance, viewing FIG. 8, seal members 92A are fittingly received in annular grooves 94 of the longitudinally extending passage 61. The inner surfaces of the seal members 92A sealingly engage the outer surface of the lead body 30 to prevent fluid from reaching the stationary contacts and the mobile contacts.

It should be understood that the foregoing description is only illustrative of the invention. Various alternatives and modifications can be devised by those skilled in the art without departing from the invention. For example, it is within the purview of the invention that in another embodiment of the invention, both of the mobile contact devices are of the set screw construction of contact 64 or that, in still another embodiment of the invention, both of the mobile contact devices are of the coil spring construction of contact 62 or that, in yet other embodiments of the invention, the set screw construction of contact 64 may be used at either location with the coil spring construction used at the complementary location. Accordingly, the present invention is intended to embrace all such alternatives, modifications and variances, which fall within the scope of the appended claims.

What is claimed is:

1. An implantable lead comprising:
   a lead body comprising a connector assembly disposed at a proximal end of the lead body, the connector assembly having a connector with terminal contacts;
   a pair of distal electrodes that are disposed on the lead body;
   a pair of proximal electrodes that are disposed on the lead body and located proximal to the distal electrodes;
   a first pair of stationary contacts in electrical continuity, respectivey, with the pair of distal electrodes;
   a second pair of stationary contacts in electrical continuity, respectively, with the pair of proximal electrodes; and
   a bifurcation boot slidably disposed on the lead body, the bifurcation boot comprising a pair of mobile contacts and conductors, wherein the pair of mobile contacts are in electrical continuity with the terminal contacts by the conductors, and wherein the mobile contacts are movable between first and second positions on the lead body such that in the first position the mobile contacts are engaged with the first pair of stationary contacts to establish electrical continuity between the terminal contacts and the distal electrodes, and such that in the second position the mobile contacts are engaged with the second pair of stationary contacts to establish electrical continuity between the terminal contacts and the proximal electrodes.

2. The implantable lead of claim 1 and further comprising:
   a first stop member integral with the lead body and engageable by the bifurcation boot to establish the first position; and a second stop member integral with the lead body and spaced from the first stop member and engageable by the bifurcation boot to establish the second position.

3. The implantable lead of claim 2 wherein:

the lead body has an outer peripheral surface;

the first stop member is a distal ring projecting radially away from the outer peripheral surface and located distally of the bifurcation boot; and the second stop member is a proximal ring projecting radially away from the outer peripheral surface and located proximally of the bifurcation boot.

4. The implantable lead of claim 1 and further comprising:

a pair of ventricular electrodes disposed on the lead body and located distally of the distal electrodes, and wherein the connector assembly comprises a pair of terminal contacts in electrical continuity with the respective ventricular electrodes.

5. The implantable lead of claim 4, wherein the pair of ventricular electrodes comprises a ventricular tip electrode and a ventricular ring electrode proximally spaced from the ventricular tip electrode.

6. The implantable lead of claim 1, and further comprising a plurality of seal members contiguously encircling the outer surface of the lead body at longitudinally spaced locations;

wherein the bifurcation boot defines a longitudinally extending passage therethrough for the slidable reception of the lead body; and wherein the seal members are engaged with the longitudinally extending passage to prevent fluid from reaching the stationary contacts and the mobile contacts.

7. The implantable lead of claim 6, wherein each of the stationary contacts on the lead body is positioned between a pair of the seal members.

8. The implantable lead of claim 6, wherein the seal members comprise O-rings.

9. The implantable lead of claim 1, wherein the pair of proximal electrodes and the pair of distal electrodes are atrial electrodes.

10. The implantable lead of claim 1, wherein the conductors are wires.

11. An implantable lead comprising:

a lead body comprising a pair of ventricular electrodes disposed at a distal region of the lead body, the lead body comprising a connector assembly disposed at a proximal end of the lead body, the connector assembly having a connector with terminal contacts;

a pair of distal atrial electrodes that are disposed on the lead body and located proximal to the ventricular electrodes;

a pair of proximal atrial electrodes that are disposed on the lead body and located proximal to the distal atrial electrodes;

a first pair of stationary contacts in electrical continuity, respectively, with the pair of distal atrial electrodes;

a second pair of stationary contacts in electrical continuity, respectively, with the pair of proximal atrial electrodes; and a bifurcation boot slidably disposed on the lead body, the bifurcation boot comprising a pair of mobile contacts and conductors, wherein the mobile contacts are in electrical continuity with the terminal contacts by the conductors, and wherein the mobile contacts are movable between first and second positions on the lead body such that in the first position the mobile contacts are engaged with the first pair of stationary contacts to establish electrical continuity between the terminal contacts and the distal atrial electrodes, and such that in the second position the mobile contacts are engaged with the second pair of stationary contacts to establish electrical continuity between the terminal contacts and the proximal atrial electrodes.

12. The implantable lead of claim 11 and further comprising:

a first stop member integral with the lead body and engageable by the bifurcation boot to establish the first position; and a second stop member integral with the lead body and spaced from the first stop member and engageable by the bifurcation boot to establish the second position.

13. The implantable lead of claim 12 wherein:

the lead body has an outer peripheral surface;

the first stop member is a distal ring projecting radially away from the outer peripheral surface and located distally of the bifurcation boot; and the second stop member is a proximal ring projecting radially away from the outer peripheral surface and located proximally of the bifurcation boot.

14. The implantable lead of claim 11, wherein the pair of ventricular electrodes comprise a ventricular tip electrode and a ventricular ring electrode proximally spaced from the ventricular tip electrode.

15. The implantable lead of claim 11, and further comprising a plurality of seal members contiguously encircling the outer surface of the lead body at longitudinally spaced locations;

wherein the bifurcation boot defines a longitudinally extending passage therethrough for the slidable reception of the lead body; and wherein the seal members are engaged with the longitudinally extending passage to prevent fluid from reaching the stationary contacts and the mobile contacts.

16. The implantable lead of claim 15, wherein each of the stationary contacts on the lead body is positioned between a pair of the seal members.

17. The implantable lead of claim 15, wherein the seal members comprise O-rings.

18. The implantable lead of claim 11, wherein the conductors are wires.

* * * * *